United States Patent
Kulkarni et al.

(10) Patent No.: US 6,528,647 B2
(45) Date of Patent: Mar. 4, 2003

(54) PROCESS FOR THE SYNTHESIS OF AN ALIPHATIC CYCLIC AMINE

(75) Inventors: Shivanand Janardan Kulkarni, Andhra Pradesh (IN); Kondapuram Vijaya Raghavan, Andhra Pradesh (IN); Radha Rani Vippagunta, Andhra Pradesh (IN); Srinivas Nagabandi, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/818,282

(22) Filed: Mar. 27, 2001

(65) Prior Publication Data

US 2002/0183517 A1 Dec. 5, 2002

(51) Int. Cl.$^7$ .................. C07D 295/00; C07D 203/00; C07D 207/323; C07D 207/06
(52) U.S. Cl. .............. 540/612; 546/184; 546/254; 548/564; 548/519
(58) Field of Search .......... 540/612; 546/184, 546/254; 548/564, 579; 564/479, 480

(56) References Cited

U.S. PATENT DOCUMENTS 3,903,079 A  9/1975 Heinz et al. ............ 260/239 B
4,739,051 A * 4/1988 Schroeder et al. .......... 544/106

OTHER PUBLICATIONS

"Selective Intramolecular Cyclization of Terminal (alpha–omega) Diamines to Saturated Heterocyclics over Modified Zeolites" Rani et al. Ind. J. Chem. Sect. A vol. 38A(3), pp. 286–290 (1999).*

"Amination of Diols and Polyols to Acyclic Amines" Fischer et al. Catalysis Today vol. 37(2), pp. 167–189 (1997).*

Rao, Y.U.S. et al, "Modified ZSM–5 Catalysts for the Synthesis of Five–And–Six Membered Heterocyclics. " J.Org. Chem., vol. 59, No. 14, (1994) pp. 3998–4000.

Matsusuzaki, T. et al. "Vapor–Phase Ammonolysis is 1–5–Pentanediol Over Silid–Acid Catalysts." Chemical Abstract No. 88: 50607 and Yuki Gosei Kag Aku Kyokaishi 35 (10) (1977) pp. 839–841.

* cited by examiner

Primary Examiner—Mukund J. Shah
Assistant Examiner—Zachary C. Tucker
(74) Attorney, Agent, or Firm—Ladas & Parry

(57) ABSTRACT

Disclosed is a process for selectively producing aliphatic cyclic amines which comprises reacting a dihydric alcohol characterized by four to six carbons, preferably 1,5-pentane diol, with excess ammonia in presence of ZSM-5 catalyst modified with group of elements nickel, copper or cobalt-containing, at a temperature of at least 250° C., wherein said catalyst incorporates at least one metal.

21 Claims, No Drawings

PROCESS FOR THE SYNTHESIS OF AN ALIPHATIC CYCLIC AMINE

FIELD OF THE INVENTION

The present invention relates to a process for the synthesis of an aliphatic cyclic amine. More particularly, the present invention relates to amino cyclization of terminal diols. In particular this invention relates to a process for the selective synthesis of cyclic imines by the amino cyclization of a hydrocarbons having from four to six carbons and which are characterized by two hydroxy groups in the terminal positions to yield a cyclic imine.

BACKGROUND OF THE INVENTION

3-Methylpiperidine is used as a vulcanization accelerator and as an additive to lubricant oil and 3-Methylpyridine is used both as a solvent and as an intermediate in the preparation of nicotinic acid. Cyclic amines are important compounds in the synthesis of drugs and for making of various reagents. Hexamethyleneimine is an important compound which is useful as an intermediate material for pharmaceuticals and agricultural chemicals, and also finds a wide range of applications as rubber vulcanization accelerators and other rubber chemicals, they are ingredients for textile lubricants, antistatic agents and finishing agents, corrosion inhibitors for metals, and modifiers or crosslinking agents for resins.

PCT application WO 90/00546 discloses the preparation of mixtures of 3-methylpiperidine and 3-methylpyridine starting from 2-methyl-1,5-diamino pentane by passing the gaseous starting material over a catalyst comprising metal oxides at 500° C.–600° C. Preferred catalysts are copper chromite, molybdenumoxide and vanadium oxide. These catalysts are preferably applied to a support. Depending on the reaction temperature, the ratio between piperidine and pyridine can be shifted to one or the other side. This patent specification also mentions the possibility of using acidic oxides, such as $SiO_2$ or silicon aluminium oxides, without further additives as catalysts. However, the yields achieved in this way are only moderate. No information is given on the catalyst activity over extended operating times.

U.S. Pat. No. 3,903,079 discloses a process for the cycloammonolysis of disubstituted alkanes containing primary amino and/or hydroxyl groups. The catalyst used is a metal aluminosilicate molecular sieve. Preferred metals are copper, palladium, manganese, nickel and chromium. The reaction was carried out in the presence of ammonia. The yields obtained were moderate. A yield of 75% was achieved in the preparation of piperidine from 1,5-pentanediol.

However, hexamethyleneimine has been obtained in small quantities from by-products which occur in the production of hexamethylenediamine by catalytic hydrogenation of adiponitrile or in the production of hexamethylenediamine by catalytic ammonolysis of 1,6-hexanediol. It has also been reported in Journal of the Chemical Society of Japan, Vol. 82, page 1701 (1961) that hexamethyleneimine was obtained in a yield of about 10% by heating hexamethylenediamine together with Raney nickel at 160° C. to 170° C., but a greater part of the product consisted of a resinous product or tar.

Chemische Berichte, Vol 96, page 924 (1963) also discloses that by heating hexamethylene diamine together with Raney nickel at 142° C.–143° C. in a solvent such as benzene, xylene or mesitylene, hexamethyleneimine is obtained in a yield of 24 to 38% (as the picrate salt), but at the same time, 1,6-bis-hexamethyleneiminohexane is formed in a yield of 12 to 47% (as the picrate salt). Furthermore, Canadian Pat. No. 920,606 (1973) discloses that hexamethyleneimine is obtained in a selectivity of 47 to 87% by contacting hexa methylenediamine with a hydrogenation catalyst at 150° C. to 250° C. in the presence of hydrogen. However, since the conversion of hexamethylenediamine is as low as 17 to 44%, a large quantity of unreacted hexamethylenediamine must be recovered by distillation. It is also necessary to reduce the amounts of by-products by adding hydrogen and ammonia during the reaction.

In an article titled "Equilibrium Conditions for Amination of Alcohols and Carbonyl Compounds", Ind. Eng. Chem. Prod. Res. Develop., 11, 3, 333–337 (1972), Josef Pasek et al. described the influence of pressure, temperature, and initial composition on the equilibrium content of primary, secondary, and tertiary amines and unsaturated compounds.

In Catalysis of Organic Reactions, Blackburn, D. W., ed., 1990, at Chapter 14, M. Ford et al. review the selective synthesis of mixed alkyl amines by amine-alcohol reactions over hydrogen phosphate.

The amination of alcohols, aldehydes, and ketones using catalysts containing nickel, copper, or both, has been also been described, for example, in U.S. Pat. Nos. 3,520,933; 4,153,581; 4,152,353; and 4,409,399. These patents relates to selective production of diamines. U.S. Pat. No. 3,270,059 discloses the production of diaminoalkanes by passing an alkanediol, alkanolamine, alkylene oxide, or alkyleneimine along with either ammonia or an alkylamine in the presence of hydrogen and at an elevated temperature over a catalyst which contains sintered cobalt or nickel. The sintering process requires extra steps and high temperatures.

U.S. Pat. No. 4,290,946 discloses the synthesis of hexamethyleneimine from the deamino cyclisation of hexamethelene diamine over the raney nickel catayst in liquid phase but it suffers from the use of ammonia and hydrogen to reduce the catalysts prior to use it.

The amination of terminal diols to corresponding diamines is a known art over the metal oxides or on supported catalysts. But they suffer to yield cyclic imines by deamination and to avoid this they require to be carried out in presence of hydrogen gas. From the foregoing references it appears there that is a need in the art for an improved method of selectively producing cyclic imines by the amination of diols instead of diamines It would be very desirable in the art if a process were available for aminating a diol which is available in large volumes. This would provide an attractive route to an added-value commodity chemical.

OBJECTS OF THE INVENTION

The main object of the present invention is to provide a process for the preparation cyclic amines from diols which can be carried out on a commercial scale and achieves high yields. The catalyst activity should be maintained over long times.

SUMMARY OF THE INVENTION

The present invention relates to a process whrein high conversion of pentane diol, hexane diol and a high yield of piperidine and hexamethylenediamine respectively is maintained in the amination reaction of diol by inhibiting the formation of diamines and amino alcohols as by-products. These diamines find large volume applications in polyamide resins as monomer/comonomers, as well as price-competitive usage in lube oils, epoties, hot melt adhesives, and surfactants. They are also be useful in fuel additives, chelating agents, fungicides, and plastic lubricants.

Accordingly, the present invention relates to a process for the synthesis of an aliphatic cyclic imine having four to six carbons, said process comprising introducing into a reactor one or more $C_4$ to $C_6$ dihydric alcohols wherein the hydroxyl groups are in terminal positions reacting said $C_4$ to $C_6$ dihydric alcohol in a solvent and in the presence of excess ammonia in the presence of a metal containing ZSM-5 catalyst at a temperature in the range of 250° C. to 400° C. and weight hourly space velocity in the range of 0.25 to 1.00 $h^{-1}$.

In one embodiment of the invention, the dihydric alcohol used is 1,4-Butane diol to obtain pyrrolidine or pyrrole.

In one embodiment of the invention, the dihydric alcohol used is 1,5-Pentane diol to obtain piperidine or pyridine.

In one embodiment of the invention, the dihydric alcohol used is 1,6-hexane diol to obtain hexamethylene imine.

In one embodiment of the invention, the solvent is selected from the group consisting of alcohols, ethers and water.

In one embodiment of the invention, the diol is introduced into the reactor in aqueous solution.

In one embodiment of the invention, the molar ratio of ammonia to hydroxyl groups is 5 to 100.

In one embodiment of the invention, the metal amount impregnated on the catalyst ZSM-5 is in the range of 1 to 10 wt %.

In one embodiment of the invention, the Si/Al ratio of ZSM-5 catalyst is in the range of 15 to 140.

In one embodiment of the invention, one or more promoters selected from the group consisting of Group VIII and Group VIB of the Periodic Table are used.

In one embodiment of the invention, the promoters are selected from the group consisting of iron, copper, manganese, nickel, cobalt, molybdenum, lanthanum and chromium.

In one embodiment of the invention, the volume ratio of diol to solvent is in the range of 1:1 to 1:5.

In one embodiment, the invention relates to a hydroamination process which comprises reacting a diol characterized by four to six carbons, preferably 1,5-pentane diol with excess ammonia in the presence of a ZSM-5 catalyst which incorporates at least one metal selected from the group consisting of nickel and cobalt, or mixtures thereof, optionally supported, or as a bulk-metal catalyst, at a temperature of at least 250° C.

In one embodiment of the invention the cyclo amination exhibits good selectivity for the desired cyclic amine and is conducted batchwise.

In another embodiment of the invention, the reactants include diols having four to six carbons and any mixtures thereof In a further embodiment of the invention, the reactants are selected from 1,4-butanediol, 1,5-pentanedioland 1,6-hexane diol.

In the preferred embodiment this invention provides a process for the selective amino cyclization of 1,5-pentane diol to yield piperidine and its homologues in one step with greater than 95% conversions and higher selectivity towards the piperidine was achieved.

DETAILED DESCRIPTION OF THE INVENTION

Cyclic imines of four to six carbons are prepared in one step from a diol, preferably in a solvent, in the presence of excess ammonia and modified ZSM-5 catalyst, at a temperature of at least 250° C. and compounds were analysed by GC and GC mass.

The amino cyclization of 1,5-pentanediol was carried out M-ZSM5 where M is from the group of elements (H, Cr, Fe, Cu, Mn, La, Pb).

The catalyst used in this invention is a modified ZSM-5 catalyst with metal ion incorporated thereon by impregnation method or ion exchange method. The ZSM-5 catalyst can be synthesized by the reported literature using tripropylamine as template, ludox silica and aluminium isopropoxide as the source of silica and aluminium. Or a commercial catalyst available from Conteka Swedan. The catalyst was tabletted by tableting machine and made to 18–30 mesh, calcined at 500° C. for several hours to get H form of the zeolite and then soaked in the metal solution of 1 to 10 wt % of metal salt (salt may be from nitrtates, carbonates, actates or any other organic complex) for several hours then the water was evaporated. And further the catalyst was calcined at 400 to 450° C. to expel the low boilers and strengthern the catalyst.

All three classes of amines were identified through a combination of GC and GC-MS/IR techniques. The feedstock used in the practice of this invention s rises a terminal diol having from four to six carbons such as 1,4 butanediol, 1,5-pentane diol and 1,6-hexanediol.

In the one-step process of this invention, the reaction takes place in the presence of excess ammonia. The nitrogen source is required to be ammonia, preferably in gaseous form. The amination conditions to be utilized suitably include the use of from 5 to 50 moles of ammonia per hydroxyl equivalent of feedstock.

A suitable catalyst comprises at least one Group VIII metal, optionally on a support. Promoters may also be used. Suitable metals include cobalt, nickel, copper, manganese, lead, zirconium and molybdenum. Particularly effective catalyst is Cu or Ni modified zeolite.

The catalyst used without the promoters are also effective for the amino cyclization. The Si/Al ratio of the supported ZSM-5 catalyst varies from 15 to 140.

The catalyst is preferably introduced into the reaction zone initially. The temperature for the one-step process should be at least about 300° C. A suitable range is from about 250° C. to about 400° C. The preferred range varies depending on the chain length of the diol.

When the reaction is conducted on a continuous basis using the described nickel or cobalt catalysts liquid feed rates may range from about 0.25 to 1.0 WHSV. A preferred range is from about 0.5 to 0.75 WHSV.

Along with cyclic amines other oxygenated cyclic products with amino alcohols and dimines are also found in the products. The products have been identified in this work by one or more of the following analytical procedures; viz, gas-liquid chromatography (GC), infrared (IR), mass spectrometry (MS), or a combination of these techniques.

The examples which are discussed below were conducted in a vapour phase down flow reactor. The feedstocks were aqueous diol solution. The WHSV was varied from 0.25 to 1.0. The preferred amino cyclization took place over a range of temperatures from about 250° C. to about 400° C. The reaction of 1,5-pentane diol was carried out with varying the Si/Al ratio from 15 to 140. As the Si/Al ratio is increased a decrease in the formation of piperidine and increase in the pyron.

By contrast, poor hydroamination of a 25% aqueous solution of 1,3-propanediol to 1,3-propanediamine was realized in Examples 12 and 13, using copper-rich and copper-cobalt catalysts of the prior art.

To illustrate the process of the invention, the following examples are given. It is understood, however, that the examples are given only in the way of illustration and are not to be regarded as limiting the invention in any way.

EXAMPLES

A pyrex glass reactor of 20 mm dia with 60 mm length down flow reaction was used for the fixed bed experiments with the 30 mm bed length of 4 g of the modified or unmodified zeolite catalyst. The ammonia source was used as gas form. The diluted diol was passed through the preheating zone in the form of gas.

Example 1

Preparation of 5 wt % of Cu-ZSM-5: 0.95 g of Copper nitrtate was dissolved in 100 ml of distilled water and then 4 g of 18–30 mesh of calcined ZSM-5 was added then the catalyst was soaked for 6 hours. The distilled water was evaporated by heating and then the catayst was calcined for 4 hr at 420° C.

Example 2

The 1.7 ml of 1,5-pentandiol and water was fed onto the catalytic bed packed with Cu-ZSM-5 in the flow rate of 2 ml/h at 280° C. temperature. The yield of piperidine is 76.4 wt % at conversion of 99.9 wt %.

Example 3

Table 1 presents a series of Runs with various modified catalysts and their product distribution at the same conditions followed in Example 2.

TABLE 1

Aminocyclisation of 1,5 penatne diol: variation of catalyst

| Catalyst | TOS (h) | Conversion of 1,5 pentane diol (%) | % Yield of products | | | |
|---|---|---|---|---|---|---|
| | | | Pyran | Piper-dine | 5-amino pentanol | Others |
| Mn ZSM-5 (30) | 4 | 99.9 | 18.5 | 67.3 | 5.9 | 8.2 |
| Co ZSM-5 (30) | 4 | 99.9 | 17.5 | 56.0 | 9.2 | 7.2 |
| Ni ZSM-5 (30) | 4 | 99.9 | 4.6 | 90.2 | 1.0 | 4.1 |
| CU ZSM-5 (30) | 3 + 4 | 99.9 | 19.0 | 62.2 | — | 18.7 |
| Zn ZSM-5 (30) | 4 | 99.9 | 14.7 | 46.7 | 14.0 | 24.5 |
| Pb ZSM-5 (30) | 3 | 99.9 | 12.7 | 81.8 | — | 5.4 |
| Zr ZSM-5 (30) | 2 | 97.6 | 29.0 | 29.0 | 18.5 | 21.1 |
| Mo ZSM-5 (30) | 4 | 91.6 | 30.6 | 19.4 | 35.0 | 6.6 |

Feed: 1,5 Pentane diol+Water: 1:3; temperature=300° C.; WHSV=0.5 h$^{-1}$; Catalyst weight=4 g; metal weight=5 wt %; in others unsaturated alcohols and aldehydes are major Example 4

The 1.7 ml of 1,5-pentandiol and water was fed onto the catalytice bed packed with Ni-ZSM-5 in the flow rate of 2 ml/h at 280° C. temperature, The yield of piperidine is 90.2 wt % at conversion of 99.9 wt %.

Example 5

The 1.7 ml of 1,5-pentandiol and water was fed onto the catalytice bed packed with Cu-ZSM-5 in the flow rate of 2 ml/h at 350° C. temperature. The yield of piperidine is 26.2 wt % at conversion of 51.4 wt %.

Example 6

The 1,4-butanediol and water in volume 1:3 ratio was fed onto the catalytic bed packed with Cu-ZSM-5 in the flow rate of 2 ml/h at 250° C. temperature. The yield of pyrrolidine is 99.0 wt % at conversion of 99.9 wt %.

Example 7

TABLE 2 represents the runs of various catalysts and their product distribution at the same conditions given in Example 6.

| Catalyst | TOS (h) | Conversion of 1,4-butanediol (%) | % Yield of products | | | | |
|---|---|---|---|---|---|---|---|
| | | | THF | Furan | Pyrrole | Pyrrolidine | Others |
| H ZSM-5 (30) | 4 | 93.3 | 23.3 | — | — | 16.0 | 54.0 |
| Cr ZSM-5 (30) | 3 | 86.1 | 52.7 | 20.3 | — | — | 13.1 |

TABLE 2-continued represents the runs of various catalysts and their product
distribution at the same conditions given in Example 6.

| Catalyst | TOS (h) | Conversion of 1,4-butanediol (%) | % Yield of products | | | | |
|---|---|---|---|---|---|---|---|
| | | | THF | Furan | Pyrrole | Pyrrolidine | Others |
| Fe ZSM-5 (30) | 4 | 99.9 | — | — | — | 95.9 | 4.0 |
| Mn ZSM-5 (30) | 2 | 95.8 | 17.5 | — | 36.2 | 27.5 | 14.6 |
| Cu ZSM-5 (30) | 4 | 99.9 | — | — | — | 99.0 | 0.9 |
| La ZSM-5 (30) | 3 | 99.9 | — | — | 93.8 | 3.0 | 3.1 |

Feed: 1,4 Butanediol+Water: 1:3; temperature=250° C.; WHSV=0.5 h$^{-1}$; Catalyst weight=4 g; metal weight=5 wt %; in others unsaturated alcohols and aldehydes are major.

Example 8

1,6-hexanediol and water in volume ratio of 1:3 was fed onto the catalytic bed packed with Cu-ZSM-5 in the flow rate of 2 ml/h at 300° C. temperature, the yield of hexamethylene imine is 68.4 wt % at conversion of 99.9 wt %.

Example 9

1,6-hexanediol and water in volume ratio of 1:3 was fed onto the catalytic bed packed with M-ZSM-5 in the flow rate of 2 ml/h at 300° C. temperature and the product distribution is given in Table 3.

TABLE 3

| Catalyst | TOS (h) | Conversion of 1,6-hexanediol (%) | % Yield of products (wt %) | | | |
|---|---|---|---|---|---|---|
| | | | Hexamethylene imine | Oxepane | 6-amino-1 hexanol | Others |
| H ZSM-5 (30) | 3 | 73.6 | 49.2 | 15.9 | 1.4 | 7.1 |
| HZSM-5 (280) | 3 | 62.8 | 34.3 | 12.8 | 10.7 | 5.0 |
| Cr ZSM-5 (30) | 3 | 99.9 | 20.3 | 58.3 | 5.9 | 15.4 |
| Cu ZSM-5 (30) | 3 | 99.9 | 30.9 | 41.4 | 4.1 | 23.5 |
| Ni ZSM-5 (30) | 3 + 4 | 98.6 | 18.6 | 28.4 | 19.6 | 32.0 |
| Ce ZSM-5 (30) | 3 | 99.9 | 88.3 | — | 4.5 | 7.1 |

Feed: 1,6 hexane diol+Water: 1:3; temperature=300° C. WHSV=0.5 h$^{-1}$; Catalyst weight=4 g; metal weight=5 wt %; in others unsaturated alcohols and aldehydes are major.

Advantages of the Invention

The present invention provides a process that comprises of environmentally clean and economical technology, easily seperable and it can be recycled and reused.

- This process provides an attractive route to the value added commodity chemicals
- This method provides a selective heterogeneous catalyst with longer life.
- This method provides a route, wherein a particular kind of product can be obtained selectively by substituting a particular metal ion.

REFERENCES

Josef Pasek et al, "Equilibrium Conditions for Amination of Alcohols and Carbonyl Compounds," Ind. Eng. Chem. Prod. Res. Develop., 11, 3, 333–337 (1972). Month unavailable.

Alfons Baiker et al., "Catalytic Amination of Long Chain Aliphatic Alcohols," Ind. Eng. Chem., Prod. Res. Dev., 16, 3, 261–266 (1977). Month unavailable.

Michael E. Ford et al., Selective Catalytic Synthesis of Mixed Alkylamines and Polyfunctional Amines, Catalysis of Organic Reactions, D. W. Blackburn, ed., Ch. 14, pp. 219–240 (1990) month unavailable.

J. F. Knifton and D. J. Janitor, "Diaminoalkane Syntheses Via Selective Amination of Hydroxy Aldehydes,"

Patent Application Serial No. 60/109,572, filed Nov. 23, 1998 (Docket No. TH-1160).

We claim:

1. A process for the synthesis of an aliphatic cyclic imine having four to six carbons, said process comprising introducing into a reactor at least one $C_4$ to $C_6$ dihydric alcohol wherein the hydroxyl groups are in terminal positions, reacting said $C_4$ to $C_6$ dihydric alcohol in a solvent and in the presence of excess ammonia in the presence of a metal impregnated ZSM-5 catalyst at a temperature in the range of 250° C. to 400° C. and weight hourly space velocity in the range of 0.25 to 1.00 h$^{-1}$ to obtain said aliphatic cyclic amine, wherein the dihydric alcohol is introduced into the reactor in aqueous solution.

2. A process as claimed in claim 1 wherein the dihydric alcohol used is 1,4-Butane diol to obtain pyrrolidine or pyrrole.

3. A process as claimed in claim 1 wherein the dihydric alcohol used is 1,5-Pentane diol to obtain piperidine or pyridine.

4. A process as claimed in claim 1 wherein the dihydric alcohol used is 1,6-hexane diol to obtain hexamethylene imine.

5. A process as claimed in claim 1 wherein the solvent is selected from the group consisting of alcohols, ethers and water.

6. A process as claimed in claim 1 wherein the molar ratio of ammonia to hydroxyl groups is 5 to 100.

7. A process as claimed in claim 1 wherein the metal amount impregnated on the catalyst ZSM-5 is in the range of 1 to 10 wt %.

8. A process as claimed in claim 1 wherein the Si/Al ratio of ZSM-5 catalyst is in the range of 15 to 140.

9. A process as claimed in claim 1 wherein one or more promoters are used selected from the group consisting of Group VIII and Group VIB of the Periodic Table.

10. A process as claimed in claim 9 wherein the promoters used are selected from the group consisting of iron, manganese, copper, nickel, cobalt, molybdenum, lanthanum and chromium.

11. A process as claimed in claim 1 wherein the volume ratio of diol to solvent is in the range of 1:1 to 1:5.

12. A process for the synthesis of an aliphatic cyclic imine having four to six carbons, said process comprising introducing into a reactor at least one $C_4$ to $C_6$ dihydric alcohol wherein the hydroxyl groups are in terminal positions, reacting said $C_4$ to $C_6$ dihydric alcohol in a solvent and in the presence of excess ammonia in the presence of a metal impregnated ZSM-5 catalyst at a temperature in the range of 250° C. to 400° C. and weight hourly space velocity in the range of 0.25 to 1.00 $h^{-1}$ to obtain said aliphatic cyclic amine, wherein the molar ratio of ammonia to hydroxyl groups is 5 to 100.

13. A process as claimed in claim 12, wherein the dihydric alcohol is 1,4-butane diol and pyrrolidine or pyrrole is obtained from the reacting.

14. A process as claimed in claim 12, wherein the dihydric alcohol is 1,5-Pentane diol and piperidine or pyridine is obtained from the reacting.

15. A process as claimed in claim 12, wherein the dihydric alcohol is 1,6-hexane diol and hexamethylene imine is obtained from the reacting.

16. A process as claimed in claim 12, wherein the solvent is selected from the group consisting of alcohols, ethers and water.

17. A process as claimed in claim 12, wherein the metal is impregnated on the catalyst ZSM-5 in an amount within the range of 1 to 10 wt %.

18. A process as claimed in claim 12, wherein the Si/Al ratio of the ZSM-5 catalyst is in the range of 15 to 140.

19. A process as claimed in claim 12, wherein the reacting is in the presence of at lest one promoter selected from the group consisting of Group VIII and Group VIB of the Periodic Table.

20. A process as claimed in claim 19, wherein the promoter is selected from the group consisting of iron, manganese, copper, nickel, cobalt, molybdenum, lanthanum and chromium.

21. A process as claimed in claim 12, wherein the volume ratio of diol to solvent is in the range of 1:1 to 1:5.

* * * * *